(12) United States Patent
Miyazaki et al.

(10) Patent No.: US 8,935,941 B2
(45) Date of Patent: Jan. 20, 2015

(54) METHOD OF CLADDING MONOLITHIC SILICA BODY AND SEPARATION MEDIUM

(75) Inventors: Shota Miyazaki, Saitama (JP);
Hiroyuki Terashima, Fukushima (JP);
Masahiko Nyudo, Fukushima (JP);
Masayoshi Ohira, Saitama (JP); Kei Morisato, Saitama (JP); Masahiro Furuno, Saitama (JP)

(73) Assignee: GL Sciences Incorporated, Tokyo (JP)

( * ) Notice: Subject to any disclaimer, the term of this patent is extended or adjusted under 35 U.S.C. 154(b) by 526 days.

(21) Appl. No.: 12/865,815

(22) PCT Filed: Feb. 1, 2008

(86) PCT No.: PCT/JP2008/052079
§ 371 (c)(1),
(2), (4) Date: Aug. 2, 2010

(87) PCT Pub. No.: WO2009/096044
PCT Pub. Date: Aug. 6, 2009

(65) Prior Publication Data
US 2011/0000279 A1    Jan. 6, 2011

(51) Int. Cl.
*B01J 20/283*    (2006.01)
*B01D 15/22*    (2006.01)
(Continued)

(52) U.S. Cl.
CPC ............ *B01D 15/22* (2013.01); *B01J 20/103* (2013.01); *B01J 20/28042* (2013.01); *B01J 20/283* (2013.01); *G01N 30/6052* (2013.01);
(Continued)

(58) Field of Classification Search
USPC .................................. 65/36; 210/198.2, 656
See application file for complete search history.

(56) References Cited

U.S. PATENT DOCUMENTS 6,412,306 B1 *   7/2002   Flieger et al. ................. 65/32.2
2003/0155676 A1   8/2003   Lubda et al.
(Continued)

FOREIGN PATENT DOCUMENTS

CN    85101444 A    4/1985
JP    2 291963 A    12/1990
(Continued)

OTHER PUBLICATIONS

International Search Report for PCT/JP2008/052079, May 1, 2008, 2 pages.
(Continued)

*Primary Examiner* — David A Rogers
(74) *Attorney, Agent, or Firm* — Hahn Loeser & Parks LLP

(57) ABSTRACT

To use a monolithic silica body in chromatography with a HPLC column or a GC column and to simplify the use thereof as a separation medium, it is intended to provide a method of cladding a main body of a monolithic adsorbent or separating agent with glass so as to protect the outer surface, and to provide a separation medium prepared by the method. To this end, a monolithic silica body alone is formed by molding, and the molding is coated with a glass body; and then the glass body and the monolithic silica body are fused and integrated at the melting temperature of the glass body at an appropriate pressure. The surface of the resulting monolithic silica body clad with glass is strongly protected by the glass, and the homogeneity of the interior of the monolithic silica body is maintained, and thus uniform flow of a sample solution ensures analytical accuracy.

20 Claims, 16 Drawing Sheets

(51) Int. Cl.
*B01J 20/10* (2006.01)
*B01J 20/28* (2006.01)
*G01N 30/60* (2006.01)
*B01J 20/32* (2006.01)
*B01D 15/20* (2006.01)
*G01N 30/50* (2006.01)
*G01N 30/52* (2006.01)

(52) U.S. Cl.
CPC ............. *B01J20/3257* (2013.01); *B01D 15/20* (2013.01); *B01J 2220/54* (2013.01); *B01J 2220/82* (2013.01); *B01J 2220/825* (2013.01); *G01N 30/50* (2013.01); *G01N 2030/528* (2013.01)
USPC ............................. 65/36; 210/198.2; 210/656

(56) References Cited

U.S. PATENT DOCUMENTS

| | | | | |
|---|---|---|---|---|
| 2005/0230298 | A1* | 10/2005 | Jiang et al. | 210/198.2 |
| 2006/0113231 | A1* | 6/2006 | Malik | 210/198.2 |
| 2008/0099389 | A1* | 5/2008 | Nagaoka et al. | 210/198.2 |
| 2008/0223786 | A1* | 9/2008 | Xu et al. | 210/656 |
| 2008/0283458 | A1* | 11/2008 | Ishii et al. | 210/198.2 |
| 2009/0001007 | A1* | 1/2009 | Shimizu et al. | 210/198.2 |
| 2009/0218267 | A1* | 9/2009 | Mori et al. | 210/198.2 |

FOREIGN PATENT DOCUMENTS

| | | |
|---|---|---|
| JP | 2002-505005 A | 2/2002 |
| JP | 2002-362918 A | 12/2002 |
| JP | 2004-503776 A | 2/2004 |
| JP | 2005-265553 A | 9/2005 |
| JP | 2006-122851 A | 5/2006 |
| JP | 2007-145636 A | 6/2007 |
| WO | 2005/072164 A2 | 8/2005 |
| WO | 2008/112702 A1 | 9/2008 |

OTHER PUBLICATIONS

EP 08 71 0958 Supplementary European Search Report dated Jun. 6, 2012.

* cited by examiner

METHOD OF CLADDING MONOLITHIC SILICA BODY AND SEPARATION MEDIUM

TECHNICAL FIELD

The present invention relates to a method of cladding a monolithic silica body which enables the monolithic silica body to be directly used as various separation columns, and a separation medium.

A method and an instrument in which glass is used as a clad for a main body of a monolithic adsorbent or separating agent are proposed. The resulting separation medium is used in an HPLC column, a GC column, a column for column chromatography, a column for pretreatment, a guard column, a cartridge for solid phase, a passive sampler or the like.

BACKGROUND ART

Separation media prepared by packing particles in a cylindrical pipe or the like have been long widely used as an HPLC column, a cartridge for solid phase, a column for column chromatography, a column for pretreatment, a GC column and the like in chromatography.

Monolithic bodies have been invented as an alternative to such particles and have attracted attention. Monolithic bodies have a three-dimensional network skeleton and advantages thereof include higher porosity and higher separation ability at low pressures than those of particles.

However, these monolithic bodies alone are easily damaged and cannot be directly used as a separation medium. Therefore, an HPLC column is produced by covering it with a cylindrical plastic pipe, or a cartridge for solid phase is produced by fixing a monolithic body on a resin chip or cartridge.

Also, capillary monolithic columns for HPLC, which are produced by forming a monolithic body within a fused quartz tube having an inner diameter of 1 mm or less, are marketed.

At present, however, these methods fail to make full use of the advantages of monolithic bodies. In the case of commercially available Chromolith (registered trademark), a cylindrical monolithic body is prepared and the surface is mechanically polished, chemically treated and clad with a PEEK pipe to produce an HPLC column.

This method is disclosed in National Publication of International Application No. 2007-292751, and focuses on the poor separation efficiency of silica monolith having a small diameter, and as a result of the studies of the cause, an uneven structure of a silica gel layer has been found on the periphery of the silica monolith. As a measure for the improvement, it is suggested to reduce the diameter by grinding the outer peripheral layer when preparing a cylindrical monolithic body.

The method is employed for forming a monolithic column using a so-called clad which coats the resulting cylindrical monolithic body, the term meaning a sealed porous monolithic molded product designed so that liquid is allowed to flow from only one end of the cylinder, not from the side. Although it is necessary to form a most stable skeleton structure to prepare a cylindrical monolithic body having a high separation ability, making the side of the cylinder perfectly curved is difficult, and part of the ideal skeleton structure is broken by mechanical processing on the side. Therefore, the method is incapable of making full use of the ability of monolithic bodies.

Even if coating with resin is successfully done without mechanical processing, such resin is mainly composed of an organic polymer and has different properties from monolithic bodies mainly composed of inorganic silica gel. With PEEK resin, for example, hydrophobic adsorption occurs.

Also, although an inorganic binder is contained so as to improve the pressure resistance, the resin and the inorganic binder cause a specific separation behavior other than that of monolithic bodies.

Further, to coat with resin, it is necessary to raise the temperature up to a point higher than the softening point of the resin, and cladding leads to degradation of a chemically treated portion, failing to demonstrate high performance.

Also, as disclosed in International Publication Nos. 99/38006 and 99/50654, there is a technique of preparing a monolith in a fused quartz capillary. In this technique, the main components are the same, and so no specific separation behavior as in resin clad is found. However, it is considered that when forming a monolith in fused quartz, the inner diameter can only be at most about 1 mm, and about 0.2 mm to achieve high performance.

In this technique, the inner surface of fused silica and sol liquid are bonded and gelled to form a monolithic body. Upon gelation, however, the volume is reduced and the portion near the inner surface of the capillary is pulled by the bonding force with the inner surface, making it difficult to form a homogeneous skeleton. In a terrible case, the monolithic body is separated from the inner surface. Due to the bonding to the inner surface, the original, stable monolithic skeleton cannot be maintained, and the resulting monolithic body has poorer properties than those synthesized using a monolithic body alone.

Japanese Patent Laid-Open No. 2007-516821 proposes a chromatography column and a capillary prepared by etching the surface of a gel mold such as glass, glass-coated stainless steel or fused quartz to increase the surface area and chemical modification, and filling the gel mold with a monomer raw material to form pores by polymerization and aging.

In this method, the inner surface of the gel mold is etched or the inner surface area is increased by forming a coat by pre-treating with solution or slurry to strengthen the contact with monomers to be packed, and so achieving close contact is impossible.

An object of this method is to reduce voids formed between the gel mold and a monolithic molded article due to the shrinking process of the monolithic molded article as much as possible so as not to decrease the efficiency of separation in chromatography.

Further, to achieve the object, it is recommended to add particles of, for example, plastic, ceramic, glass or inorganic oxide of Ti, Al or Zr to reduce shrinkage of monolithic molded articles.

In addition, the publication also describes a method of using glass as the gel mold. However, even this method requires a step of etching the inner surface of the glass mold. Therefore, for strengthening the contact between the monomer and the mold as described above, it is not possible to achieve close contact between the two or to integrate them, and so the void formed between them still affects the separation ability.

DISCLOSURE OF THE INVENTION

To solve the above problems of conventional arts, by preparing a monolithic body first and then coating it with glass having the same composition as the monolithic body, specific separation behaviors for other than $SiO_2$ are eliminated, and the monolithic body and the glass are integrate to form a strong skeleton. Moreover, chemical treatment after coating with glass makes the monolithic body and the glass inner surface homogeneous, providing a separation medium capable of achieving extremely high analytical performance.

Monolithic bodies have a large surface area and are porous with mesopores and through pores, and therefore are highly capable of holding chemical components. It is desired that the glass clad, on the other hand, has a small surface area and is not porous and do not hold chemical components, and this ensures high performance analysis.

To solve the above problems and achieve the object, the present invention first provides a method of cladding a monolithic silica body, comprising coating a side surface of a monolithic silica body molded into a rod shape with a glass body having the same main component as the monolithic silica body and fusing the monolithic silica body and the glass body at the melting temperature of the glass body at an appropriate pressure.

Second, the method of cladding a monolithic silica body according to the above method, wherein the side surface of the monolithic silica body molded into a rod shape and the glass body are fused entirely or in some part is proposed.

Third, the method of cladding a monolithic silica body according to the above method, wherein fusing the monolithic silica body molded into a rod shape and the glass body with which the side surface of the monolithic silica body is coated is flexibly controlled by temperature is proposed.

Fourth, the method of cladding a monolithic silica body according to the above method, wherein the side surface of the monolithic silica body molded into a rod shape is coated with the glass body, and then the monolithic silica body is subjected to chemical modification is proposed.

Fifth, a method of cladding a monolithic silica body, comprising coating a side surface of a monolithic silica body molded into a rod shape with a glass body and then subjecting the monolithic silica body to chemical modification is proposed.

Sixth, a separation medium prepared by coating a side surface of a monolithic silica body molded into a rod shape with glass having the same main component as the monolithic silica body and fusing the two is proposed.

Seventh, the separation medium according to the above separation medium, wherein all or part of the side surface of the monolithic silica body molded into a rod shape is fused with glass is proposed.

Eighth, a separation medium prepared by coating a side surface of a monolithic silica body molded into a rod shape with a glass body and then subjecting the monolithic silica body to chemical modification is proposed.

Ninth, the separation medium according to the above separation medium, wherein an opening is formed on at least one end of the monolithic silica body is proposed.

Tenth, the separation medium according to the above separation medium, wherein a protective layer is formed on the outside of the glass is proposed.

Eleventh, the separation medium according to the above tenth separation medium, wherein a coat layer is formed between the outside of the glass and the protective layer is proposed.

Twelfth, the separation medium according to the above separation medium, wherein the protective layer is composed of one member selected from metal and synthetic polymer or a mixture thereof is proposed.

Thirteenth, the separation medium according to the above separation medium, wherein the coat layer contains a synthetic polymer is proposed.

Fourteenth, the separation medium according to the above separation medium, wherein the separation medium is any one of a HPLC column, a GC column, a column for a column chromatography, a column for pretreatment, a guard column, a cartridge for solid phase and a passive sampler is proposed.

Fifteenth, a method of analysis, comprising using any one of the above separation media is proposed.

According to the present invention, only by coating a monolithic silica body with a glass body and employing appropriate temperature and pressure, the monolithic silica body and the glass body can be integrated very easily to achieve cladding without other physical or chemical coating methods.

Thus, this is the easiest way to clad a monolithic silica body. Further, the exterior of the resulting clad monolithic silica body is strongly protected and the homogeneity of the interior and the exterior is firmly maintained.

As a result, the exterior of the separation medium is strongly protected, and chemical treatment in the production process is easy, providing a structure in which the homogeneity of the interior and the exterior is maintained.

Moreover, since surface modification and chemical modification follow the cladding step in the present invention, a large amount of monolithic silica bodies can be chemically treated, and so production is very efficient.

BEST MODE FOR CARRYING OUT THE INVENTION

Figure 1:
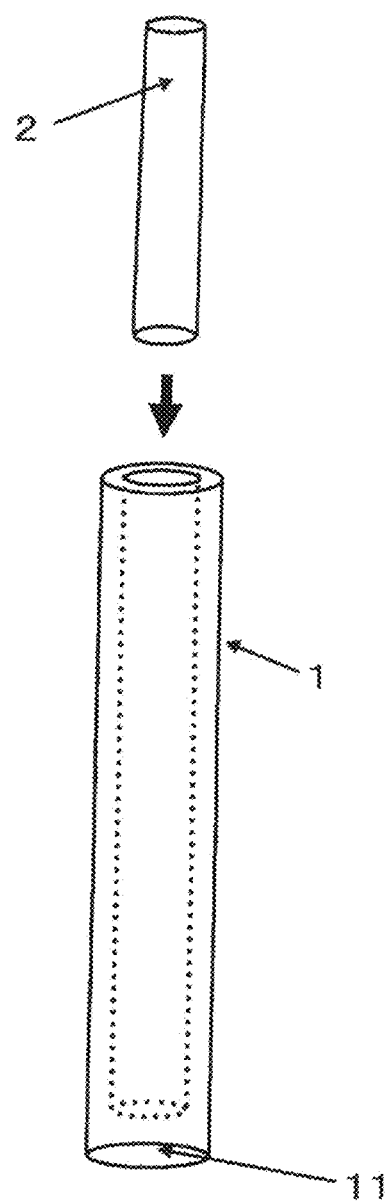
FIG. 1 is an explanatory view of a first step of the method of the present invention.
Figure 2:
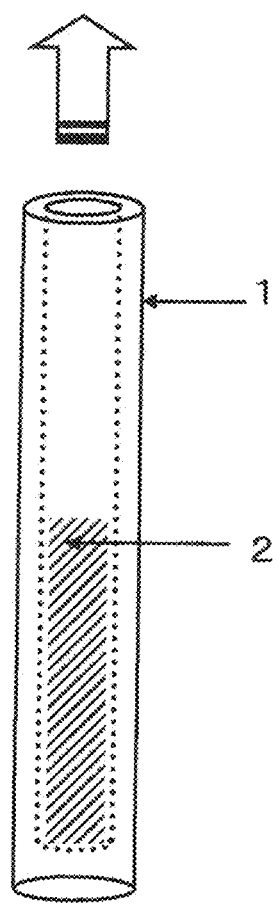
FIG. 2 is an explanatory view of a second step of the method of the present invention.

In the following, the present invention will be described in more detail. The present invention relates to a method of cladding a monolithic silica body, comprising preparing a monolithic silica body by molding in a rod shape, coating the monolithic silica body with a glass body and adhering and assimilating the two, and a separation medium prepared by the method.

To prepare a monolithic body, a conventionally known sol-gel method is used. Specifically, the monolithic silica body is prepared by a sol-gel method including addition of a surfactant and hydrolysis of tetraethoxysilane. By converting into sol at about 40° C. in a polycarbonate pipe which is unreactive to tetraethoxysilane, a soft monolithic sol body is prepared. The skeleton is formed at this stage.

Thus, to form a homogeneous skeleton, this solating step is most important. When preparing in a fused silica capillary, chemical bonding with silanol on the inner surface occurs simultaneously in the solating step, making it difficult to form a homogeneous skeleton. For this reason, it is necessary to prepare a monolithic body independently to achieve high performance.

Upon solation, the through pore skeleton through which a mobile phase flows is determined, and then mesopores which affect the surface area are formed on the surface of the skeleton. They are formed by dissolving a part of the skeleton with an alkaline solution or the like. A separation medium having mesopores of 60 to 600 A and a surface area of 100 to 800 m$^2$/g is preferred as a separation medium for chromatography, but this is not particularly limited.

Next, to stabilize the skeleton formed, the resultant is baked. Baking is performed at 300 to 1250° C., preferably 400 to 900° C. at which little structural change occurs. In the present invention, as long as monolithic bodies are prepared by baking at 400° C. or higher, they serve all purposes, and the method of synthesis or reagents are not particularly limited.

The technique of the sol-gel method is based on descriptions detailed in Japanese Patent Laid-Open No. 2002-362918, Anal. chem. 420 A (2001) and N. Tanaka et al. Monolithic Column.

The homogeneity of the structure of a monolith column is very important to maintain the performance of the column. Typically, the diameter of the skeleton, through pores, mesopores and gel densities are relevant to the structure.

The homogeneity of the interior and the exterior of the column is particularly important. It is required that the homogeneous monolithic structure is not lost when cladding with glass, and the temperature of adhesion and homogenization of glass upon glass cladding is sufficiently lower than the temperature at which crosslinking of metal oxide proceeds (polymerization degree) so as not to affect the homogeneous monolithic structure.

Conventionally, the monolithic body is subjected to chemical treatment and then coated with resin to form a column. In the present invention, however, the monolithic body is first coated with glass and integrated, and then subjected to chemical treatment of so-called surface modification and chemical modification.

For example, by putting a cylindrical monolithic body in a glass tube and treating so that the side of the monolithic body adheres to the glass tube with increasing or reducing pressure at a temperature near the melting temperature of the glass tube, a cylindrical monolithic separation medium whose side is coated with glass is prepared.

Types of glass include hard glass, soft glass, low melting point glass, Pyrex and ceramic. As long as they contain $SiO_2$ as a main component, any of them may be used after changing the softening temperature.

Generally, the softening temperature is changed depending on the amount of metal in the composition. Therefore, it is necessary to adjustment temperatures based on materials. For example, the treatment may be performed at 400 to 500° C. for low melting point glass or at 700 to 800° C. for Pyrex glass.

The temperature and the pressure are adjusted at about 0.1 to 10 atm. The method is not particularly limited as long as the side of the monolithic body homogeneously adheres to glass.

An example of glass coating methods for forming glass clad is shown in FIG. 1. A glass tube (2.4 mm i.d.×4 mm o.d.) 1 whose one end is closed is prepared.

Monolithic gel 2 prepared as described above (about 2.20 to 2.39 mm i.d., slightly smaller than the inner diameter of 2.4 mm i.d. of the glass tube 1) is put in the glass tube 1. Next, the glass tube 1 is heated while evacuating to 100 to 380 Torr using a vacuum pump. The temperature may be about 730° C. for hard glass and about 530° C. for soft glass.

It is required that the wall material (glass clad) is hard and has a sufficiently higher smoothness than the monolithic skeleton which serves as a separation medium and a sufficiently small surface area than the monolith so as not to have the ability to hold analyte, and can maintain adhesion without expansion due to its hardness when used under high pressure. High molecular weight polymer materials such as PEEK (hydrophobic) are expanded under high pressure, and so mobile phase may flow through the channel formed between the monolithic column and the wall material.

It is necessary that glass and a monolithic silica body have good compatibility (wettability: small surface tension) and the glass and silica in the monolithic skeleton adhere under an appropriate pressure when glass is melted without the glass intruding into through pores.

Also, monolithic columns do not necessarily have a smooth cylindrical surface. Although they are of course porous and have micron size through pores, they have irregularities of a larger size on the surface. It is important to adhere the two so as to fill the irregularities.

In glass cladding, the diameter of a column is not particularly limited. This technique, however, is particularly effective for semi-micro columns having an inner diameter of less than 3 mm (the amount of flowing mobile phase being a few hundred µl/min). The smaller the column diameter, the more influential the wall surface of the column, and so the technique has a profound effect.

For the composition of glass, hard glass such as Pyrex containing a smaller amount of metal is suitable. In particular, when used for a HPLC column, using high metal content soft glass may cause adsorption of basic compounds.

Preferably, when the inner surface of glass and the side of a monolithic body are assimilated, higher performance can be achieved. Irregularities are formed on the side of the monolithic body, and if polished as in a conventional method, the skeleton is broken at that part to reduce the performance.

As described in the present invention, only by allowing glass having the same composition to physically adhere to a monolithic body, physical strength such as pressure resistance is improved compared to that of conventional materials. Further, the side of monolith and the inner surface of glass are assimilated by controlling temperature conditions, and so there is no impact on separation media.

This can be achieved only when $SiO_2$ which is the main component of glass and monolith is bonded and assimilated with each other. As described above, a glass phase is consequently formed on the side of the assimilated separation medium unlike monolithic silica body alone, and therefore the separation medium has significantly increased physical strength. The separation medium is impact resistant and can be extremely easily handled compared to using monolith alone.

Such a separation medium can also be directly subjected to severe chemical treatment. For example, when chemically treating a large number of monolithic bodies at one time in a solution, some part of conventional bare monoliths may be broken upon contact with each other, and thus stirring is impossible.

The glass bonded monolithic body according to the present invention has sufficient strength, can be stirred, is more homogeneous and can be easily treated even by a severe chemical treatment.

Further, since it can be handled as a glass body, severer chemical treatment at 200° C. or higher becomes possible. Since there is no resin part in the present invention as in conventional materials and the glass body itself can also be chemically treated as well as the monolithic body, chemical treatment can be uniformly done and the resulting data is stable.

The present invention also has a feature that a monolithic body is subjected to chemical modification after glass cladding. The chemical treatment is performed using an octadecyl group for reversed phase partition chromatography used in common HPLC, or a functional group for ion exchange, and their types are not limited.

Monolithic columns are as soft as chalk, and therefore when chemically treated in a large amount, columns collide with each other and are broken. This will not occur when they are previously clad with glass.

Also, since glass has the same structure (containing silanol group: Si—OH), the wall surface material and the monolithic column have similar properties after the chemical reaction, and this is advantageous for analysis (PEEK clad is hydrophobic and therefore may adsorb hydrophobic substance when the column is used for ion exchange or the like).

For the chemical treatment, a method of heating to reflux in an organic solvent such as toluene or dodecane using a silane agent such as alkylchlorosilane including octadecyltrichlorosilane, octadecylmethyldichlorosilane, octadecyldimethylchlorosilane, octadecyl silazane, octadecyltrimethoxysilane, octadecylmethyldimethoxysilane, octyl, trimethylchlorosilane (TMS), dimethyl-n-octylchlorosilane and dimethyl-n-octadecylchlorosilane (ODS), alkylalkoxysilane including trimethylmethoxysilane, dimethyl-n-octylmethoxysilane and dimethyl-n-octadecylmethoxysilane (ODS), aminoalkoxysilane including aminopropyltriethoxysilane, phenylalkoxysilane including phenyltrimethoxysilane, or epoxy containing silane (glycidoxypropyltrimethoxysilane), or high temperature reaction (Japanese Patent No. 2611545) may be employed.

A monolithic body clad with glass alone is sufficient to be used as a separation medium. Since a pressure resistance of about a few MPa, which is the pressure resistance of glass, can be achieved, the monolithic body can be used as a column for medium pressure chromatography, a column for gas chromatography, a solid phase column and a HPLC guard column.

Further, if a protection tube is attached so as to be adapted to HPLC which requires high pressure, the monolithic body can also be used for that purpose.

Since glass is adhered to the surface of the monolith, the mobile phase closely and uniformly flows through the monolith without the influence of the wall surface even under high pressure employed in HPLC. The pressure resistance of glass can be improved by increasing the thickness of glass or changing the glass composition.

However, increasing the thickness results in an increase in the outer diameter of the column, making handling such as chemical treatment difficult. Also, glass containing $SiO_2$ as a main component, which is similar to monolith, is desired.

To have a pressure resistance of 12 MPa or more, a protective layer may be formed. Although the glass clad monolithic body is homogeneous, it breaks when high pressure is applied to only some part. Such pressure is dispersed and pressure resistance is achieved only by uniformly covering the side with a protective layer.

Metal or synthetic polymer is used as the above protective layer. As the metal, stainless steel, titanium or iron is used. As the synthetic polymer, synthetic resin such as PEEK, polypropylene, polyethylene, Teflon (registered trademark) or polycarbonate is used. In addition to the above, a mixture of metal and synthetic polymer (for example, acrylic resin or ionomer resin containing copper or zinc) is also useful as the protective layer.

For example, a resin layer is formed on the side by inserting a glass clad monolithic body into a PEEK tube made of resin, or by heating. These protective layers allow the column to have a pressure resistance of about 28 MPa.

Further, since metal pipe such as stainless steel pipe, titanium pipe or iron pipe has a high pressure resistance of 30 MPa or more, a highly pressure resistant column can be prepared by a method in which the side of glass is mechanically polished after cladding to increase the smoothness, inserting the clad material into such an inelastic metal pipe under heating and rapidly cooling.

Although the material after glass cladding can be treated like glass and various methods can be employed, mechanical polishing is expensive, and there is a concern of a decrease in the performance of the glass monolithic body due to heating and rapid cooling. Therefore, a coat layer is disposed between the glass monolithic body and the metal pipe to provide a high performance, highly pressure resistant column at a low cost.

The coat layer itself may not be pressure resistant as long as it is disposed between the monolithic body and the metal pipe. Therefore, various synthetic resins including synthetic polymer such as epoxy resin, acrylic resin, polypropylene resin and nylon resin may be used.

Furthermore, pressure resistance can be increased by winding metal fiber on the glass monolithic body or by adding glass particles, silica gel or metal particles to various resins.

It is recommended to consider that in HPLC columns using an organic solvent, the coat layer does not come into contact with mobile phase at the inlet and outlet.

For example, a monolithic body coated with glass is put in a stainless steel tube, and a thermoplastic polymer such as epoxy resin containing silica gel particles is poured into and hardened in the space between the stainless steel tube and the monolithic body.

Next, both ends are cut to an appropriate length and a filter and a connection joint are attached. When protected in this way, a pressure resistance of 60 MPa or more can be achieved and the column is matched for high pressure HPLC.

Figure 3:
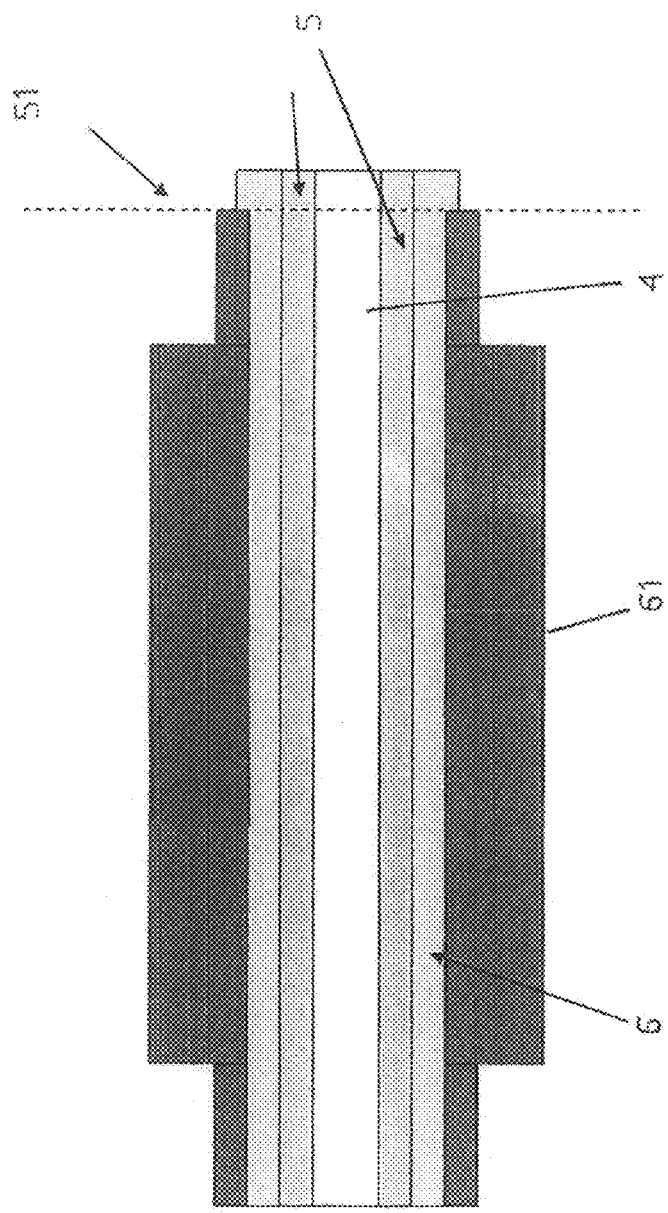
FIG. 3 is a vertical sectional explanatory view of an example of the present invention.
Figure 3:
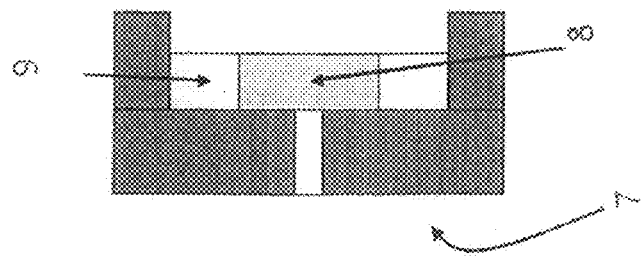

FIG. 3 shows an example of a highly pressure resistant column prepared by protecting a glass clad monolithic silica body with a stainless steel protection tube. A monolithic silica body prepared by forming glass coat 5 on a silica monolith 4 (having a diameter of, for example, 2.4 mm) is inserted into a stainless steel jacket 61 (for example, 4 mm i.d. or 4.6 mm i.d.), and an epoxy resin, a PEEK resin, water glass or silica (glass) particles 6 are put between the glass coat 5 and the stainless steel jacket 61, and is heated and cured. Then one end is cut 51 and a joint 7 is attached to the other end.

A filter 8 and a packing 9 made of Teflon (registered trademark) may be attached to the joint 7 according to need.

EXAMPLE 1

The technique of the present invention is compared with a technique of preparing a monolith in a fused silica capillary.

In the present invention, 2.4 g of polyacrylic acid (HPAA available from Sigma-Aldrich Co., average molecular weight: 100,000 Dalton, average polymerization degree: 1390) was dissolved in 4.0 g of 1M nitric acid and 1.0 g of formamide, and 6.51 g of tetraethoxysilane was added to the solution and the mixture was mixed for 10 minutes to hydrolyze tetraethoxysilane.

The solution was poured into a cylindrical container having an inner diameter of 3 mmφ, and the whole container was sealed and kept at 40° C. for 2 days to cause phase separation and gelation. The solvent of the resulting gel was substituted with 1.5 M ammonia solution, and the solution was kept at 110° C. for 4 hours. Then the gel was dried in the air at 40° C. for 2 days and heat treated at 600° C. for 5 hours.

The resulting monolithic silica body was put in a low melting point glass pipe having an inner diameter of 3 mm, and the pressure was reduced to 180 Torr by a vacuum pump (made by IWAKI CO. LTD.), and the monolithic silica body was coated with glass at 430° C. to prepare a glass-coated monolithic separation medium. The separation medium was heated to reflux and stirred in a 10% octadecyltrimethoxysilane/dodecane solution to give an octadecylated glass coated monolithic separation medium.

Figure 4:
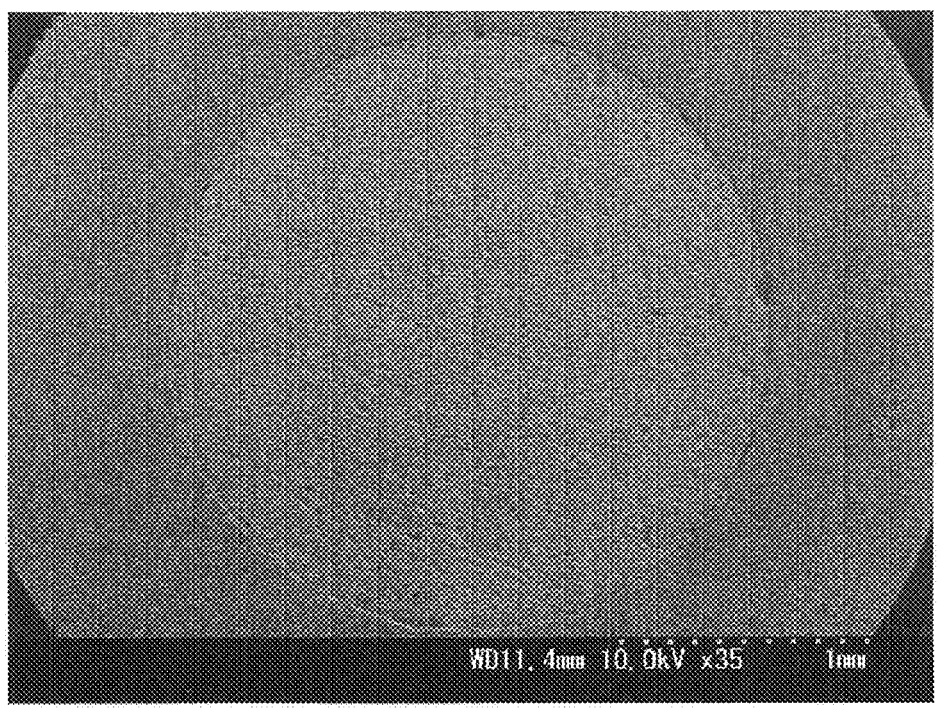
FIG. 4 is a vertical sectional micrograph of an example of the present invention.

When a monolithic silica body without glass coating was subjected to the same treatment, the monolithic silica body was broken by stirring and could not be used as a separation medium. This proves that chemical treatment was successful only when coated with glass. An electron micrograph of the octadecylated glass coated monolithic separation medium is shown in FIG. 4.

The figure shows that the monolithic silica body and the glass coating each maintain homogeneity and the degree of the adhesion of the two is excellent in the present invention.

Figure 6:
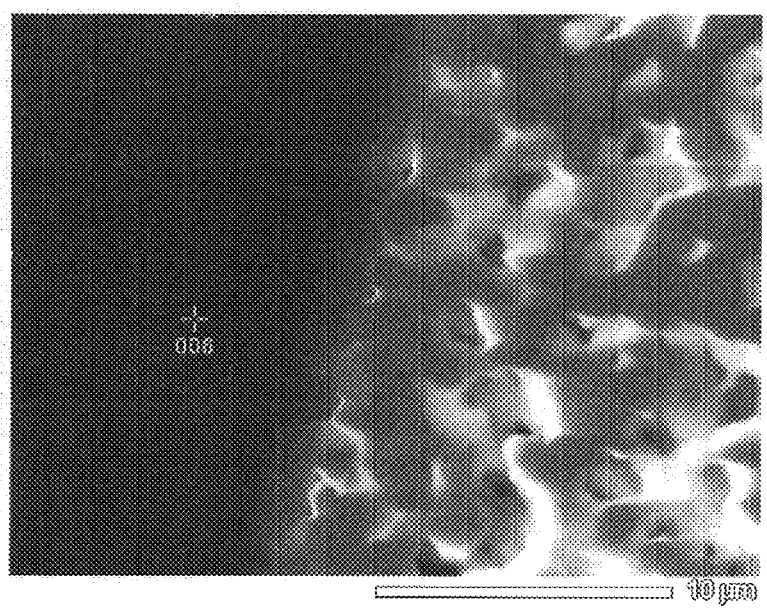
FIG. 6 is a partial enlarged micrograph of an example of the present invention.
Figure 7:
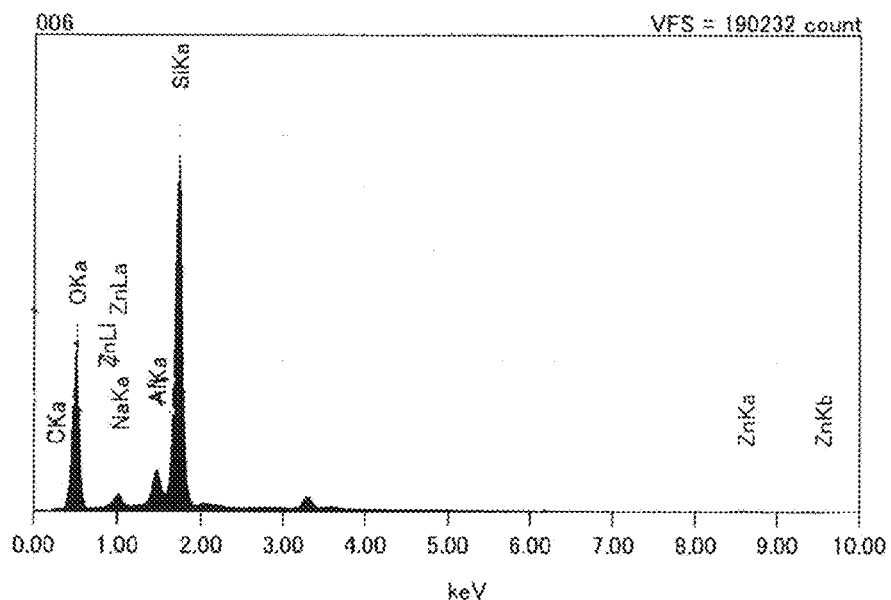
FIG. 7 is a partial X-ray analysis spectrum of an example of the present invention.
Figure 9:
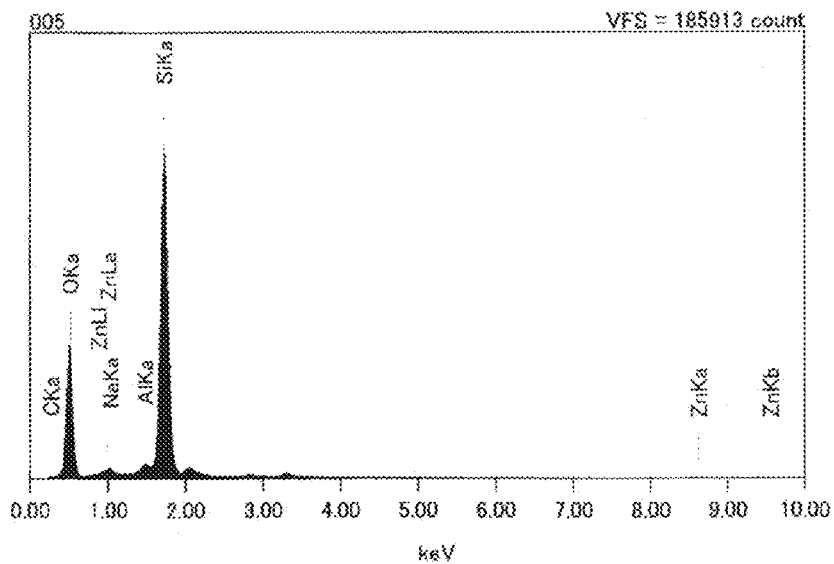
FIG. 9 is a partial X-ray analysis spectrum of an example of the present invention.

Furthermore, to support this, FIG. 6 shows an electron micrograph of a part near the boundary of the two and FIG. 7 shows a spectrum of X-ray analysis based on ZAF method simple analysis at a viewpoint A on the glass coating side. FIG. 9 shows a spectrum of X-ray analysis based on ZAF method simple analysis at a viewpoint B on the boundary of the glass coating and the monolithic silica body in an electron micrograph 8 which is similar to the electron micrograph 6.

Conditions of Electron Micrographs 6, 8, 10
Device: 6380 (LA)
Accelerating voltage: 15.00 kV
Magnification: 5,000 times
Date of measurement: Jan. 9, 2008
Pixel: 512×384
Measurement Conditions of X-rays Analysis
Device: 6380 (LA)
Accelerating voltage: 15.00 kV
Irradiation current: 1.00000 nA
PHA Mode: T2
Elapsed time: 364.46 sec
Effective time: 300.00 sec
Dead time: 17%
Counting rate: 12888 cps
Energy range: 0 to 20 keV Also, FIG. 10 shows an electron micrograph similar to the electron micrograph 6, and FIG. 11 shows a spectrum of X-ray analysis as described above at a viewpoint C of the monolithic silica body.

Figure 8:
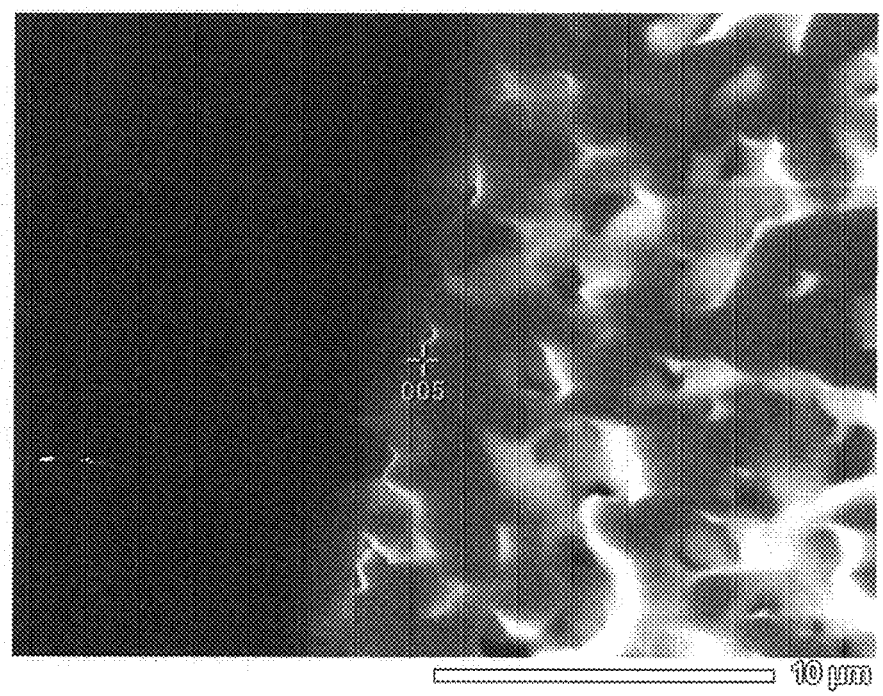
FIG. 8 is a partial enlarged micrograph of an example of the present invention.
Figure 10:
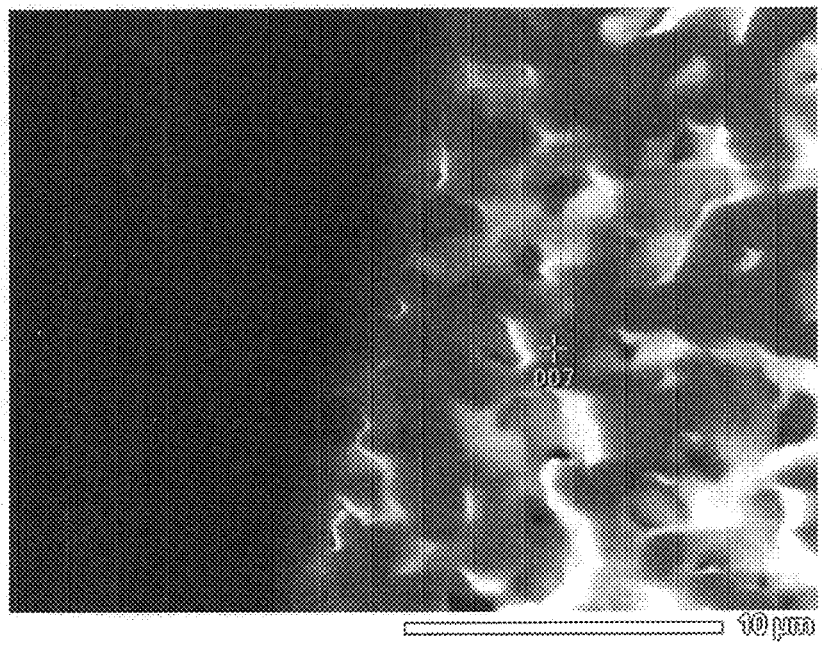
FIG. 10 is a partial enlarged micrograph of an example of the present invention.
Figure 11:
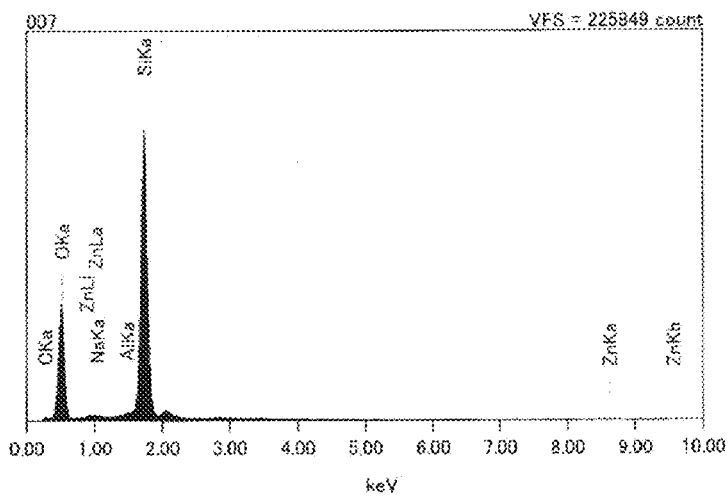
FIG. 11 is a partial X-ray analysis spectrum of an example of the present invention.

The X-ray spectra at viewpoints A, B and C show that metals derived from soft glass (Na, Al etc) are transferred to the monolithic body side of the joint part, and the measurement results at points +006 in FIG. 6, +005 in FIG. 8 and +007 in FIG. 10 clearly show the movement of components of the glass body and the monolithic body, proving that the two are integrated.

Next, the above octadecylated glass coated monolith was put into an empty stainless steel HPLC column having an inner diameter of 4 mm and an a length of 100 mm, and an epoxy adhesive (clear epoxy) was poured into the space between the monolithic body and the stainless steel and the coat layer was cured by leaving at room temperature for 12 hours.

Then both ends were cut and a packing, a filter and a joint were attached so as to avoid the contact between the coat layer and the mobile phase to prepare a highly pressure resistant HPLC column.

On the other hand, as a conventional method, a sol of 6.75 g of tetramethoxysilane, 2.25 g of methyltrimethoxysilane, 1.0 g of PEG, 2.0 g of urea and 20 mL of 0.01 N acetic acid was put in a fused capillary having an inner diameter of 0.2 mm and solated at 40° C. Methyltrimethoxysilane is necessary for reducing contraction of gel, and so monomers to be used are limited in order to prepare a monolithic silica body within a fused silica capillary as in the conventional method.

Figure 5:
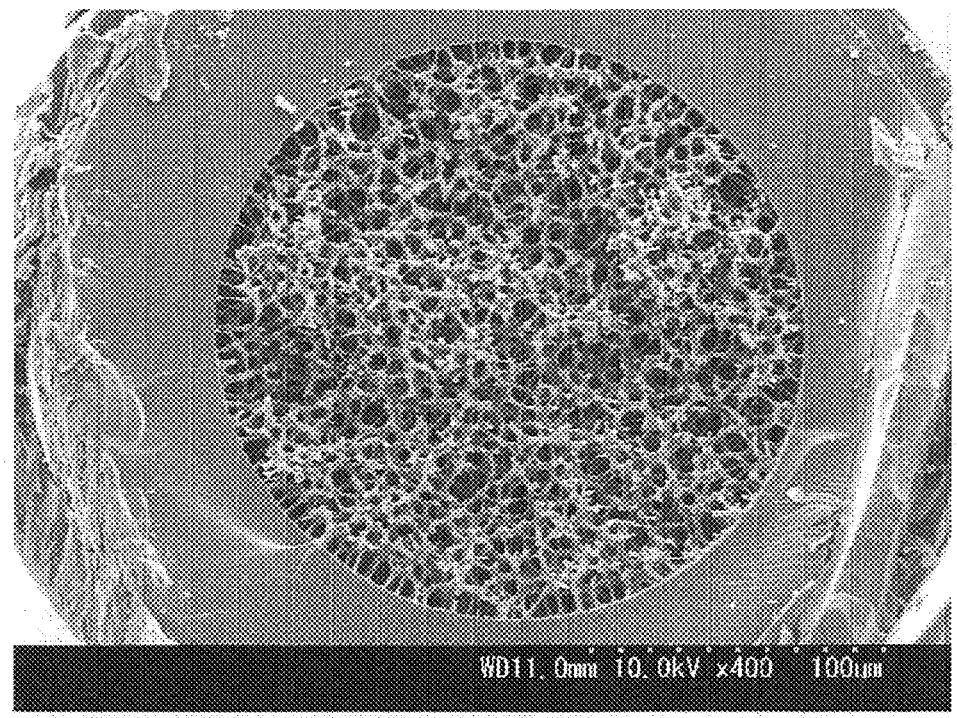
FIG. 5 is a vertical sectional micrograph of a conventional example.

Then the resultant was washed and baked at 300° C. to prepare a monolithic capillary column. An electron micrograph of the column is shown in FIG. 5.

It will be understood that the micrograph shows that the edge of the monolithic silica body is extended and deposited to the fused silica capillary to destroy the homogeneity of the structure of the monolithic silica body, forming a large vacancy which is not the structure of the monolithic silica body between the two that are in contact with each other. A uniform flow of sample solutions cannot be expected in such structure. Fused silica capillary are heat resistant up to 300° C. and so the temperature cannot be raised higher than that. Therefore, the column prepared above is physically weaker than monolithic bodies prepared by baking at 400° C. or higher as in the present invention. The column has low heat resistance to be used as a HPLC column.

Octadecylsilazane was allowed to flow to be octadecylated and end capping was performed using HMDS to prepare an ODS monolithic capillary column for HPLC.

As shown in the electron micrograph 5, the structure of the conventional column prepared by a conventional method is deformed at portions near the tube wall. On the other hand, as shown in the electron micrograph 5, the monolithic body according to the present invention has a homogenous structure from one edge to the other.

Also, the pressure resistance of the two columns, the column of the present invention and the conventional column, was examined. When a 50% aqueous methanol solution was allowed to flow at a constant pressure of 25 MPa, both the conventional column and the column of the present invention had no problem. When the pressure was set at 30 MPa, part of the monolithic body in the conventional column slipped out after 6 hours. The column of the present invention had no problem even at 60 MPa.

EXAMPLE 2

The behavior of elution of pyridine, a basic compound, was examined using the column of Example 1 of the present invention and a commercially available HPLC monolithic column clad with PEEK resin.

Although pyridine sharply eluted before phenol in the column of the present invention, tailing of pyridine peak and phenol peak is observed in the conventional column. It is considered that since a chemically treated monolithic body is clad with resin, the resin is not treated and highly hydrophobic in the conventional column, and so the shape of peaks of water-soluble compounds such as pyridine and phenol became poor due to the hydrophobic difference between the inside and portions near the tube wall.

It is also considered that chemically treated portions have been degraded upon cladding with resin to allow silanol faces to be exposed, affecting the shape of peaks.

In the present invention, since the monolithic body is coated with glass having the same main component as the monolithic body, there is no hydrophobic effect, and also since the monolithic body is chemically treated after coating, there is no effect of silanol adsorption, and so elution is sharp.

Figure 12:
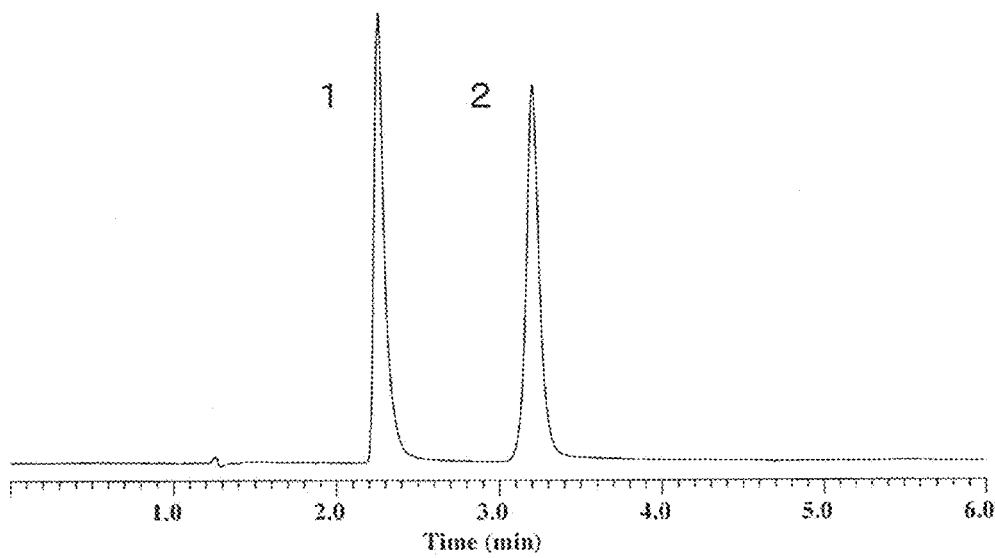
FIG. 12 is a chromatogram showing an elution pattern of an example of the present invention.
Figure 13:
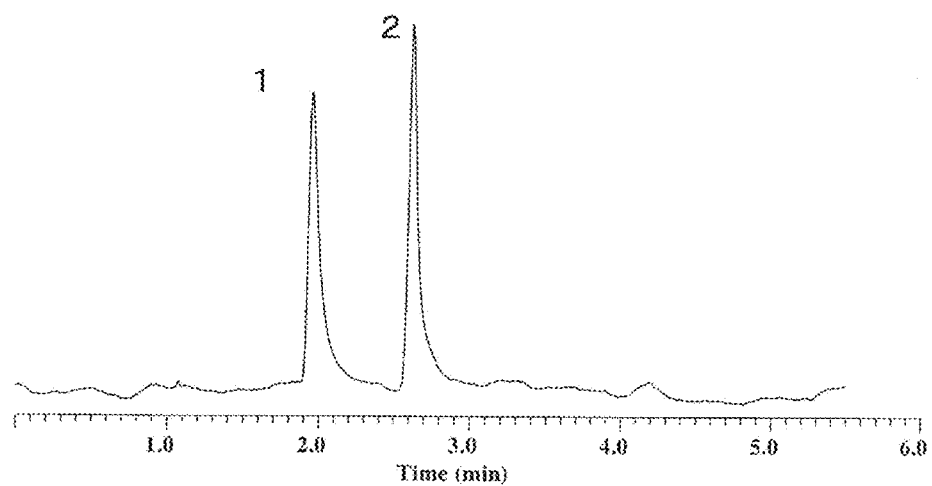
FIG. 13 is a chromatogram showing an elution pattern of an example of a conventional column.

FIGS. 12 and 13 illustrate chromatograms showing the elution behavior of pyridine of the column of the present invention and the conventional column. The column of the present invention (2.3 mm i.d.×76 mm) shown in the chromatogram of FIG. 12 has sharp peaks at a flow rate of 0.2 mL/min, although there is slight tailing of peak 1 of pyridine and peak 2 of phenol.

In conventional Chromolith (registered trademark) (3 mm i.d.×100 mm) shown in the chromatogram of FIG. 13, there is a long tailing of the peak 1 of pyridine at a flow rate of 0.5 mL/min, and the height of the peak is insufficient. Moreover, tailing of the peak 2 of phenol is also observed.

EXAMPLE 3

The identification (normal phase) of the performance of clad glass depending on the difference in fusing temperatures when using Pyrex glass was performed as follows. Fusing at 650° C. has been proved to be unsatisfactory because no peak was found. Fusing at temperatures higher than that has been proved to be satisfactory because peaks of samples were found. The highest theoretical plate number was obtained at 725° C. It is thought that at temperatures of 760° C. or higher, the monolithic silica skeleton is influenced by contraction due to the high temperature, and therefore the theoretical plate number is decreased.

The above shows that the Pyrex glass body and the monolithic silica body are firmly fused at 700 to 800° C., providing a column which can be put into practical use.

As described above, the best result was obtained at 725° C. in this Example. It is considered that the result is close to the ideal, complete assimilation of the inner surface of glass and the side of the monolithic body.

However, the column can be practically used as long as the inner surface of glass and the side of the monolithic body are partly assimilated. It is thought that assimilation occurs within the above temperature range (700 to 800° C.). As described in Example 1, the transfer of Na, Al ions derived from glass can also indicate the occurrence of assimilation of the glass inner surface and the side of the monolithic body.

While Pyrex glass was used in this Example, the temperature at which assimilation starts varies depending on the composition of glass, and the temperature is not limited to the above range. When the compositions of glass are the same, assimilation starts in a constant temperature range, and therefore the state of assimilation can be controlled according to the purpose to prepare an ideal glass clad column.

Figure 14:
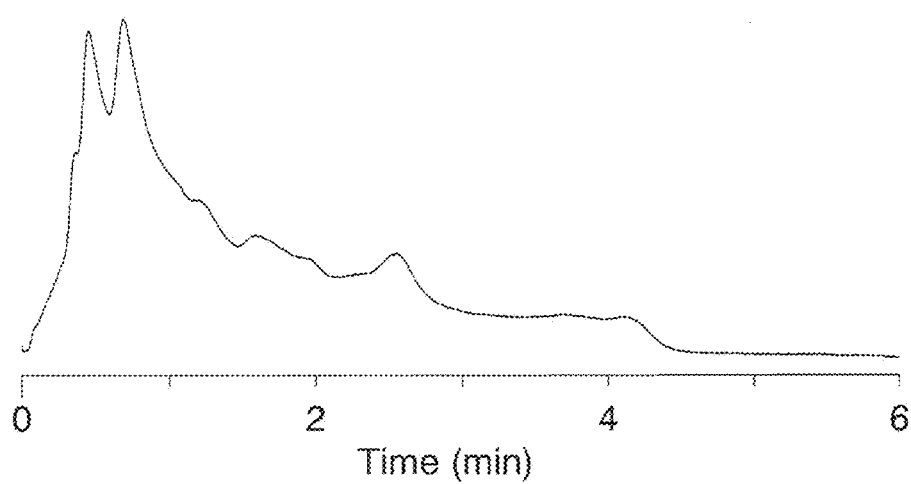
FIG. 14 is a chromatogram obtained in a temperature variation test of an example of the present invention.

FIG. 14 shows a chromatogram obtained as a result of the test at 650° C.

Figure 15:
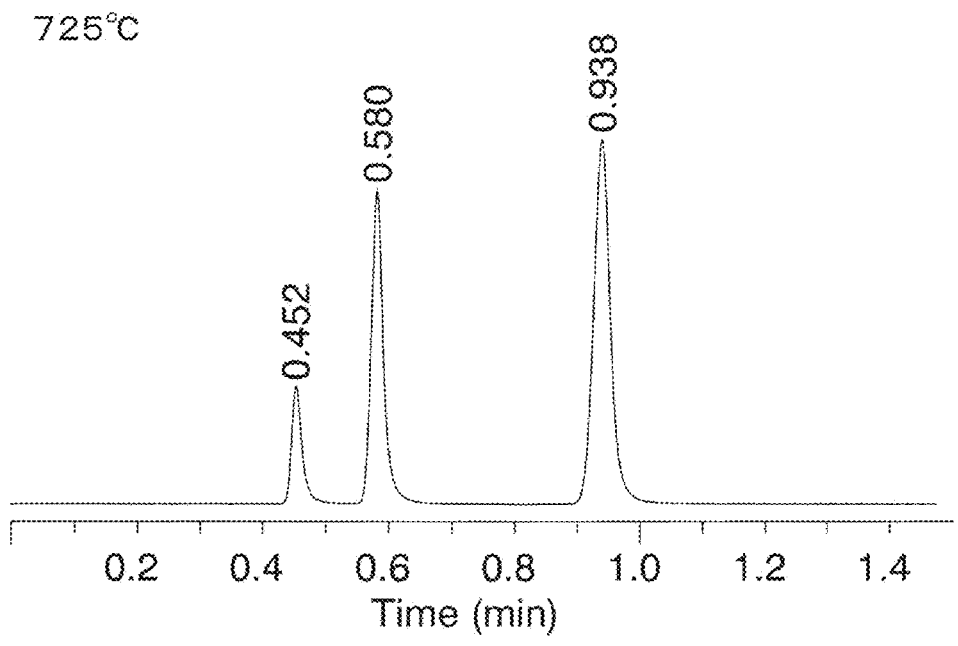
FIG. 15 is a chromatogram obtained in a temperature variation test of an example of the present invention.

FIG. 15 shows a chromatogram obtained as a result of the test at 725° C.
Flow rate: 0.4 mL/min
Pressure: 28 kgf
Length: 50 mm
Theoretical plate number: 6252.12
Symmetry: 1.08

Figure 16:
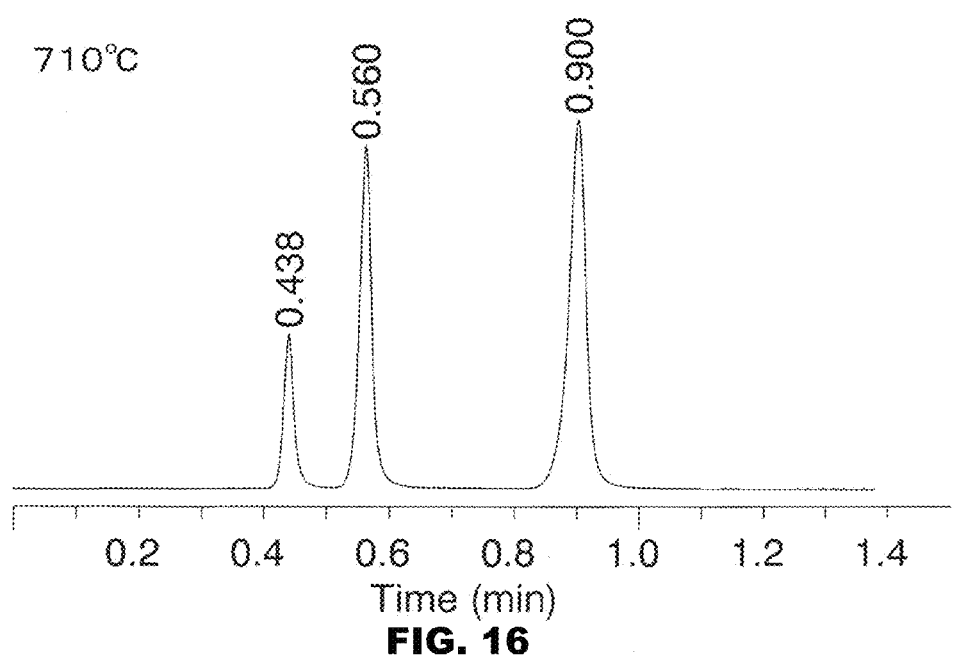
FIG. 16 is a chromatogram obtained in a temperature variation test of an example of the present invention.

FIG. 16 shows a chromatogram obtained as a result of the test at 710° C.
Flow rate: 0.4 mL/min
Pressure: 10 kgf
Length: 50 mm
Theoretical plate number: 5597.63
Symmetry: 0.91

Figure 17:
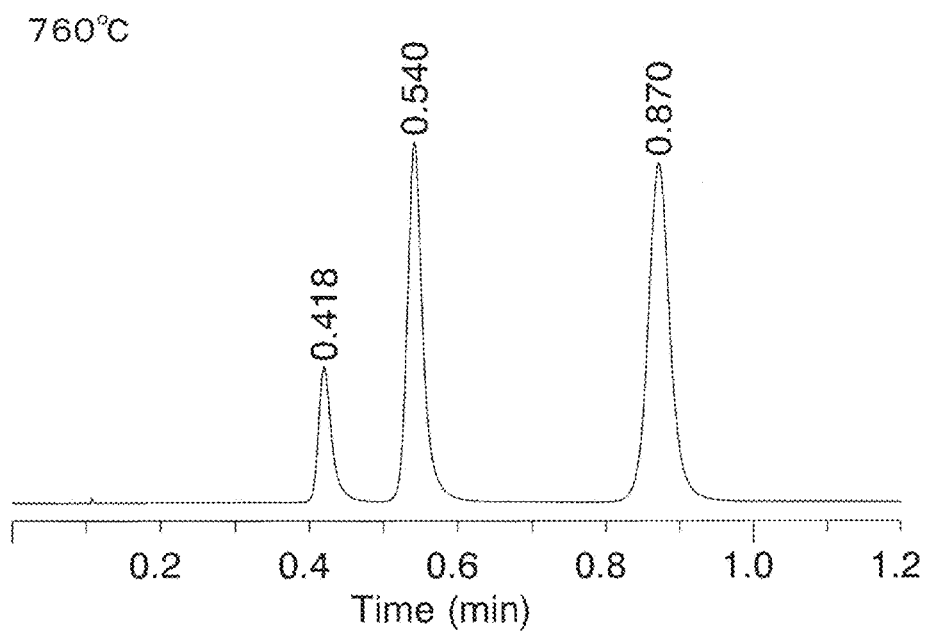
FIG. 17 is a chromatogram obtained in a temperature variation test of an example of the present invention.

FIG. 17 shows a chromatogram obtained as a result of the test at 760° C.
Flow rate: 0.4 mL/min
Pressure: 11 kgf
Length: 50 mm
Theoretical plate number: 4379.67
Symmetry: 1.12

Figure 18:
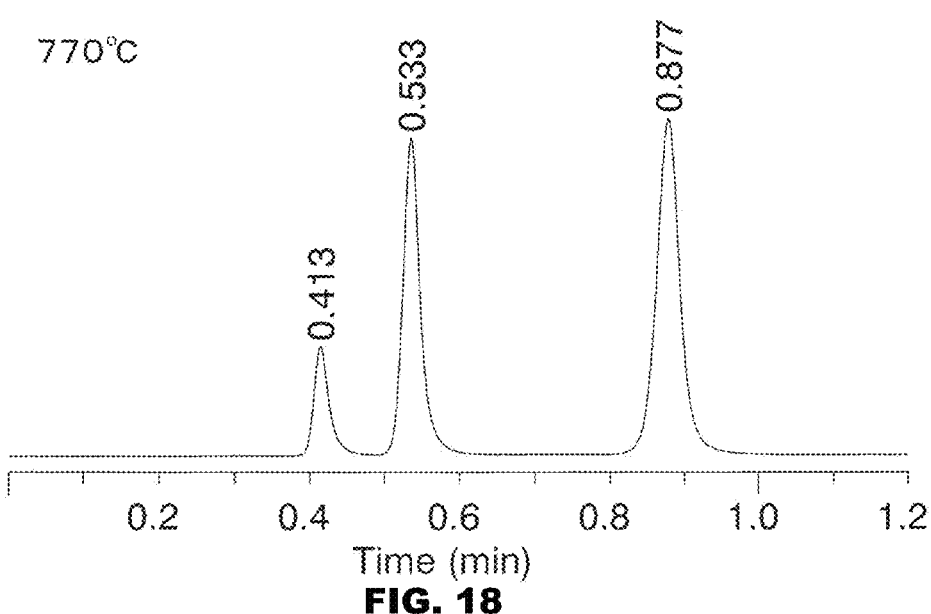
FIG. 18 is a chromatogram obtained in a temperature variation test of an example of the present invention.

FIG. 18 shows a chromatogram obtained as a result of the test at 770° C.
Flow rate: 0.4 mL/min
Pressure: 11 kgf
Length: 50 mm
Theoretical plate number: 4068.28
Symmetry: 1.07

Figure 19:
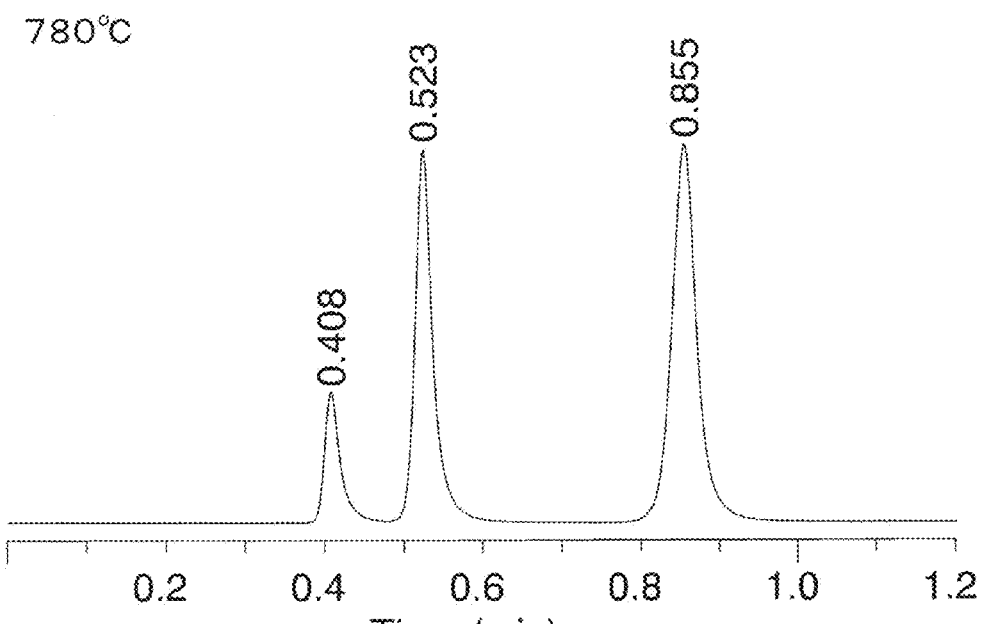
FIG. 19 is a chromatogram obtained in a temperature variation test of an example of the present invention.

FIG. 19 shows a chromatogram obtained as a result of the test at 780° C.
Flow rate: 0.4 mL/min
Pressure: 11 kgf
Length: 50 mm
Theoretical plate number: 3878.57
Symmetry: 1.07

Figure 20:
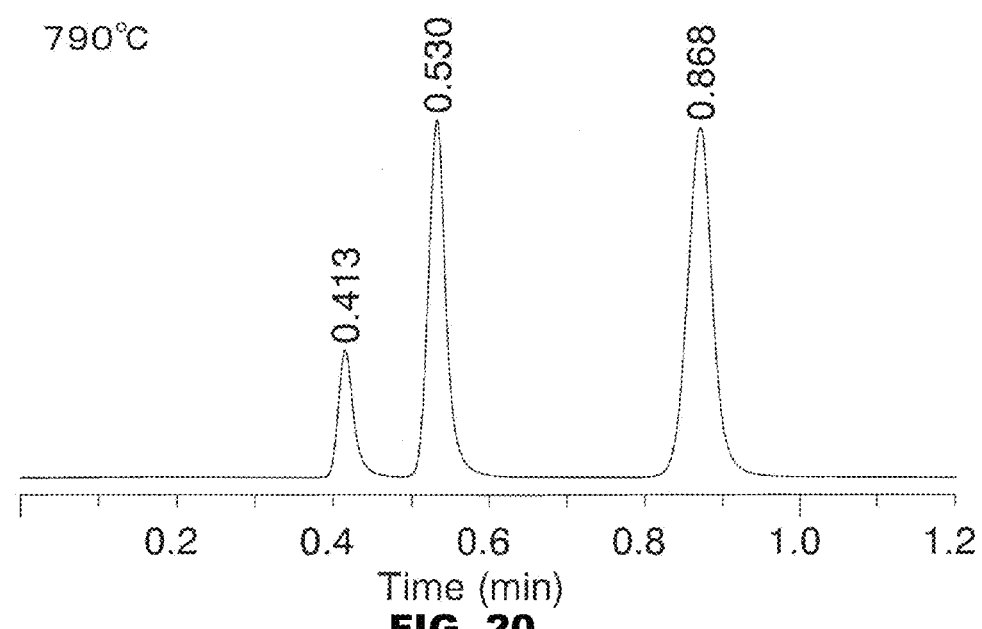
FIG. 20 is a chromatogram obtained in a temperature variation test of an example of the present invention.

FIG. 20 shows a chromatogram obtained as a result of the test at 790° C.
Flow rate: 0.4 mL/min
Pressure: 11 kgf
Length: 50 mm
Theoretical plate number: 3725.72
Symmetry: 1.08

EXAMPLE 4

Using monolithic gels having the same composition (K-18-1)(prepared in Example 1), columns coated with glass or PEEK containing the gels which were subjected to the same chemical treatment were compared based on a reverse phase test.

Figure 21:
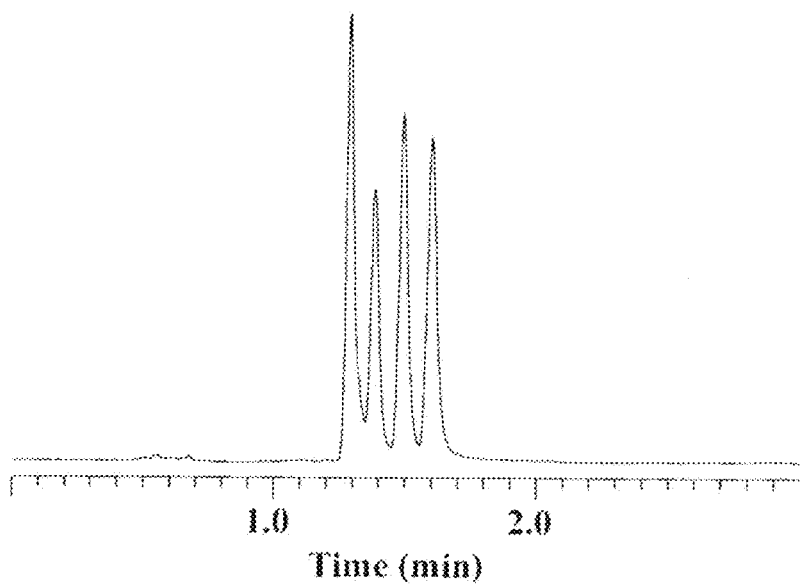
FIG. 21 is a chromatogram obtained by using an example of the present invention.
Figure 22:
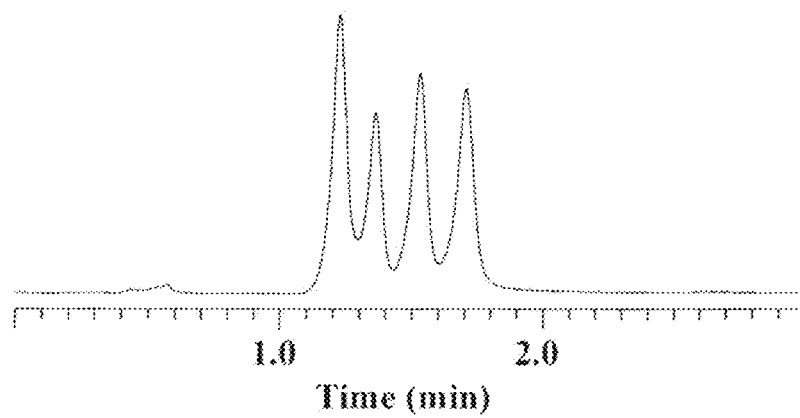
FIG. 22 is a chromatogram obtained by using a conventional example corresponding to the present invention.

FIG. 21 shows a chromatogram obtained using the glass coated column under following conditions. All peaks were sharp.
  Column: K-18-1
    Glass coat
    2.4 mm i.d.×100 mm
  Eluate: 65% acetonitrile
  Flow rate: 0.3 mL/min
  Oven temperature: 40° C.
  Detector: UV 254 nm
  Analytes: 1. Acetophenon
    2. Benzene
    3. Toluene
    4. Naphthalene On the other hand, in FIG. 22 showing a chromatogram obtained using the column coated with PEEK, tailing was found in all peaks and the theoretical plate number was low. Moreover, it was found that it took much time before the baseline became stable. This seems to be because of the hydrophobicity of the cladding material resin and because of the degradation of the chemically treated portions upon cladding.
  Column: K-18-1
    PEEK coat
    2.4 mm i.d.×82 mm
  Eluate: 65% acetonitrile
  Flow rate: 0.3 mL/min
  Oven temperature: 40° C.
  Detector: UV 254 nm
  Analytes: 1. Acetophenon
    2. Benzene
    3. Toluene
    4. Naphthalene

EXAMPLE 5

Using monolithic gels having the same composition, the performance of columns coated with glass or PEEK was compared based on a normal phase test.

Comparison between columns coated with glass or PEEK (normal phase)

Figure 23:
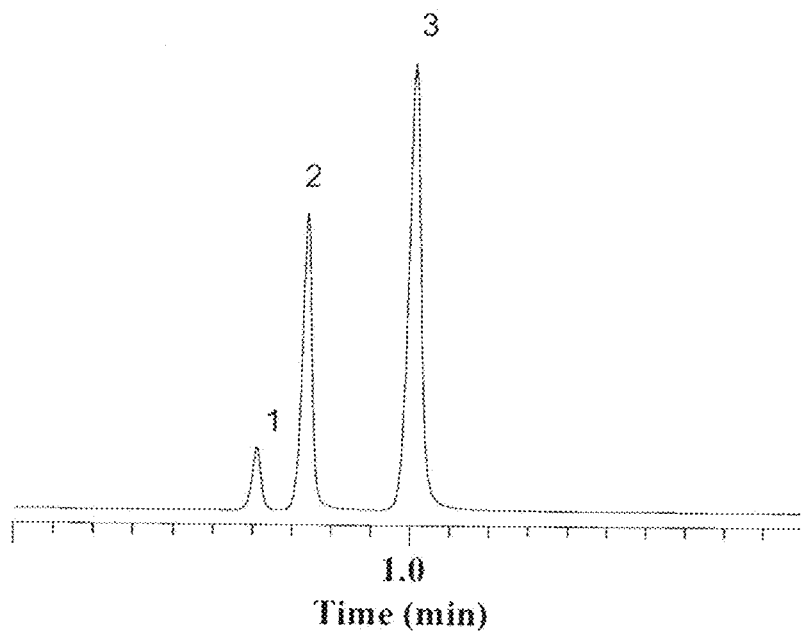
FIG. 23 is a chromatogram obtained by using a conventional example corresponding to the present invention.

As a result of the test of the column coated with PEEK under the following conditions, a chromatogram shown in FIG. 23 was obtained.
  Column: K-18-1
    PEEK coat
    2.4 mm i.d.×82 mm
  Eluate: Hexane/Ethanol=95/5
  Flow rate: 0.5 mL/min
  Oven temperature: 40° C.
  Detector: UV 254 nm
  Analytes: 1. Benzene
    2. Nitrobenzene
    3. o-Nitroanisole
  0.5 mL/min
  $N_3$=5349
  N/m=65232

The result shows a leading of the benzene peak. The peak had a symmetry of 0.95. It took as much as about 60 minutes before the baseline became stable.

Figure 24:
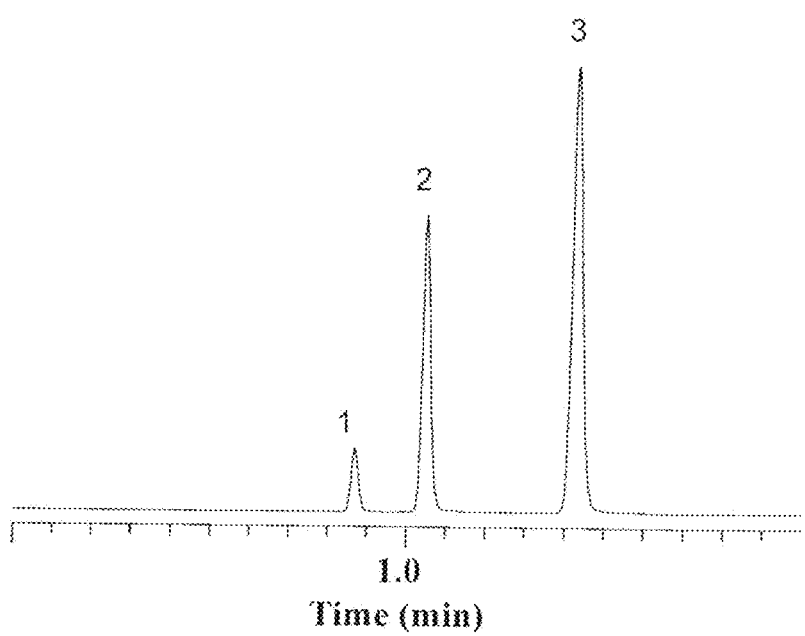
FIG. 24 is a chromatogram obtained by using an example of the present invention.

On the other hand, the test conditions of column coated with glass are as follows. A chromatogram shown in FIG. 24 was obtained. As shown in the figure, the peaks have good symmetry. The baseline became stable in about 5 minutes, and so there are distinct differences between them.
  Column: K-18-1
    Glass coat
    2.4 mm i.d.×100 mm
  Eluate: Hexane/Ethanol=95/5
  Flow rate: 0.5 mL/min
  Oven temperature: 40° C.
  Detector: UV 254 nm
  Analytes: 1. Benzene
    2. Nitrobenzene
    3. o-Nitroanisole
  0.5 mL/min
  $N_3$=14154
  N/m=141540

EXAMPLE 6

A column of the present invention chemically treated after glass cladding was compared with a conventional monolithic body prepared by cladding after chemical treatment. 4 g of polyethylene glycol (average molecular weight: 10,000) was dissolved in 40 mL of a 0.01M aqueous acetic acid solution, and 12 g of tetraethoxysilane was added to the solution and the mixture was mixed for 10 minutes to hydrolyze tetraethoxysilane.

The solution was poured into a cylindrical container having an inner diameter of 10 mmφ, and the container was sealed and kept at 40° C. for 2 days to cause phase separation and gelation. The solvent of the resulting gel was substituted with 1.5 M ammonia solution, and the solution was kept at 110° C. for 4 hours.

Then the gel was dried in the air at 40° C. for 2 days and heat treated at 600° C. for 5 hours to prepare a monolithic body having a surface area of 190 m²/g and a mesopore diameter of 10 nm.

The monolithic body was clad with glass at 725° C. in the same manner as in Example 1.

The two of the above glass clad body and a monolithic body without glass cladding were gradually heated in a 10% aminopropyltriethoxysilane toluene solution at 60° C. for 24 hours to give an aminopropyl-modified glass clad body and an aminopropyl-modified monolithic body.

The aminopropyl-modified monolithic body was put in a PEEK tube to be clad by reducing pressure at 360° C. Both ends of the two clad bodies were trimmed and a diffusion board and a connection joint made of Teflon were attached thereto to prepare columns for column chromatography.

Figure 25:
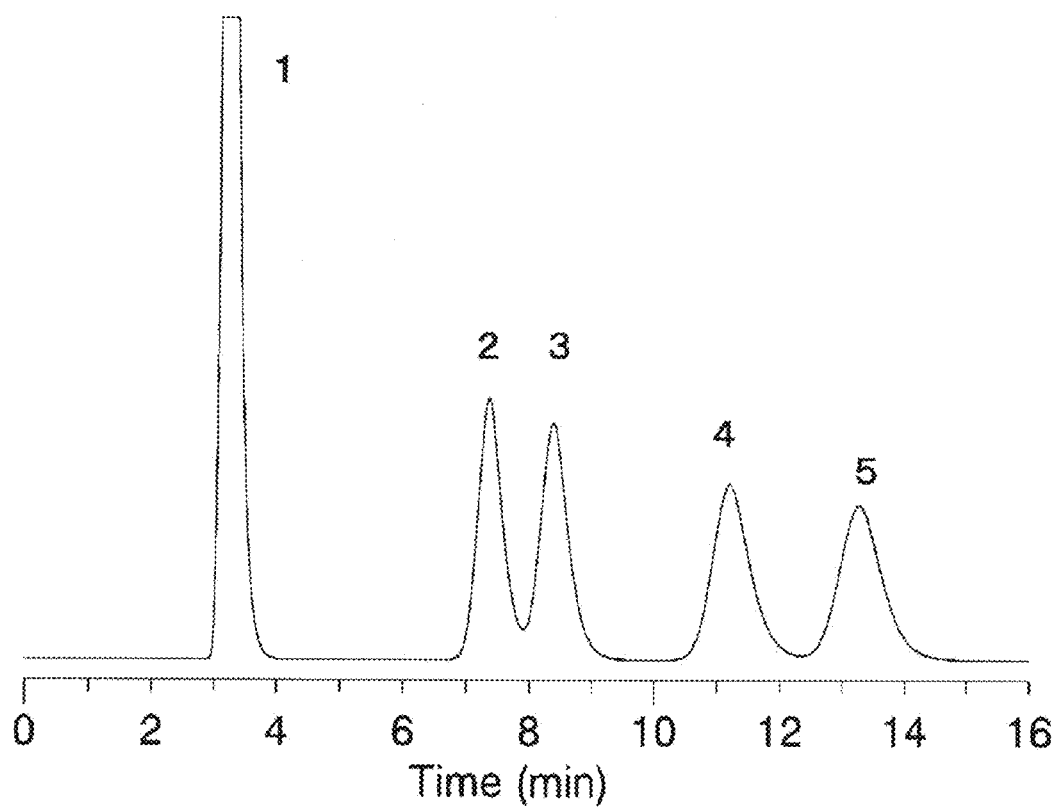
FIG. 25 is a chromatogram obtained by using an example of the present invention.
Figure 26:
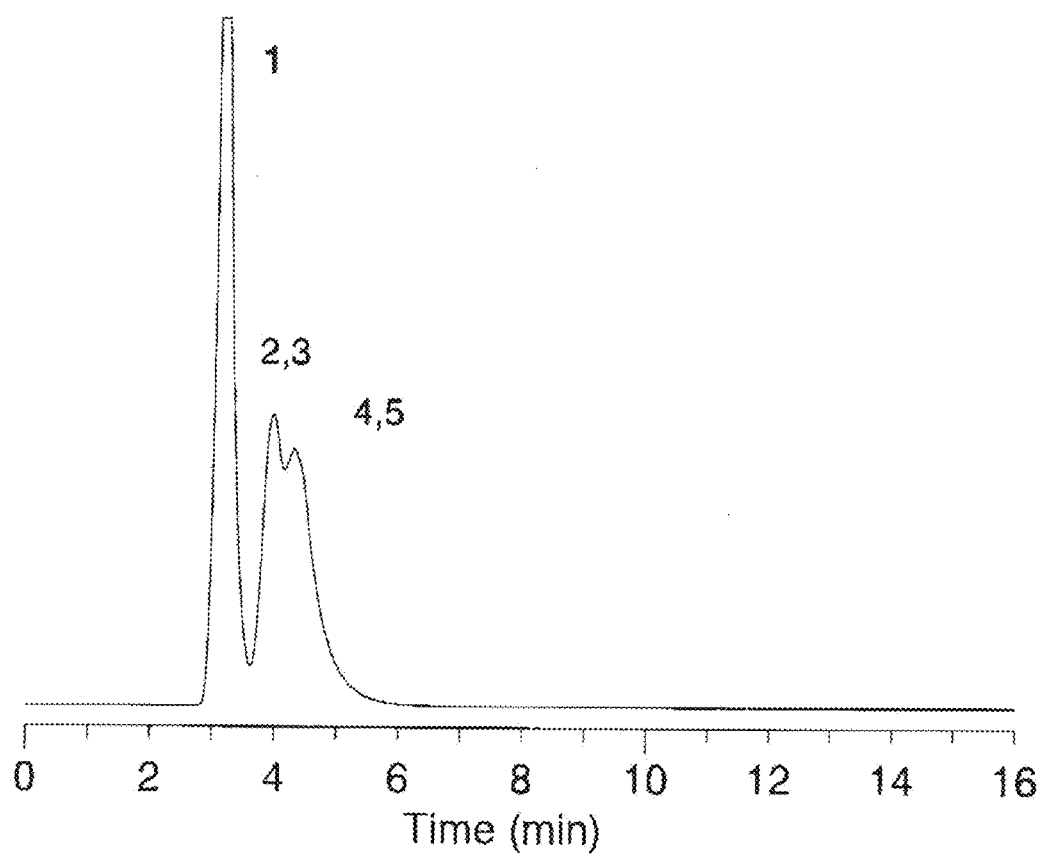
FIG. 26 is a chromatogram obtained by using a conventional example corresponding to the present invention.

The column of the present invention and the conventional column were tested under the following conditions and chromatographs were obtained. In the column for column chromatography clad with aminopropyl-modified glass prepared by chemically treating after glass cladding as in the method of the present invention, separation of sugar is successful as shown in FIG. 25. In the column prepared by chemically treating the monolith and then cladding at 230° C. as in the conventional method, separation of sugar is unsuccessful because of thermal denaturation of the chemically treated portions during cladding as shown in FIG. 26.

The above test has proved that preparing a column by glass cladding and then chemically treating as in the present invention is effective for maintaining high performance.
  Column size: 6.4 mm i.d.×100 mm
    Eluate: 80% acetonitrile
    Flow rate: 2 mL/min
    Oven temperature: room temperature
    Detector: Refractive Index (RI)
    Analytes: 1. Solvent
      2. Fructose
      3. Sucrose
      4. Glucose
      5. Maltose

INDUSTRIAL APPLICABILITY

According to the present invention, only by coating a monolithic silica body with a glass body and employing appropriate temperature and pressure, the monolithic silica body and the glass body can be integrated very easily to achieve cladding without other physical or chemical coating methods.

Thus, this is the easiest way to clad a monolithic silica body. Further, the exterior of the resulting clad monolithic silica body is strongly protected and the homogeneity of the interior and the exterior is firmly maintained.

As a result, the exterior of the separation medium is strongly protected, and chemical treatment in the production process is easy, providing a structure in which the homogeneity of the interior and the exterior is maintained.

Moreover, since surface modification and chemical modification follow the cladding step in the present invention, a large amount of monolithic silica bodies can be chemically treated, and so production is very efficient.

The invention claimed is:

1. A method of cladding a monolithic silica body, the method comprising providing a rod-shaped monolithic silica body having $SiO_2$ as a main component, coating the monolithic silica body with a glass body having the same main component as the monolithic silica body, and fusing the monolithic silica body and the glass body at the melting temperature of the glass body at a predetermined pressure to provide an integrated monolith silica body and glass body, and chemically bonding $SiO_2$ of the monolithic silica body and $SiO_2$ of the glass body with each other, thereby assimilating the monolithic silica body and the glass body with each other.

2. The method of cladding a monolithic silica body according to claim 1, wherein the step of fusing the monolithic silica body and the glass body is flexibly controlled by temperature.

3. The method of cladding a monolithic silica body according to claim 1, wherein the side surface of the monolithic silica body is coated with the glass body, the monolithic silica body and the glass body are fused and then the monolithic silica body is subjected to chemical modification to provide a chemically modified, homogeneous, glass-clad monolithic silica body.

4. A method of cladding a monolithic silica body according to claim 1, wherein the appropriate pressure is 0.1 to 10 atm.

5. A method of cladding a monolithic silica body according to claim 4, wherein the glass body is a hard or soft glass body, and fusing the monolithic silica body and the glass body at 400 to 530° C. of the melting temperature of the soft glass body for the soft glass body or at 700 to 800° C. of the melting temperature of the hard glass body for the hard glass body.

6. A method of cladding a monolithic silica body according to claim 1, wherein the glass body is a hard or soft glass body, and fusing the monolithic silica body and the glass body at 400 to 530° C. of the melting temperature of the soft glass body for the soft glass body or at 700 to 800° C. of the melting temperature of the hard glass body for the hard glass body.

7. The method of cladding a monolithic silica body according to claim 1, wherein the monolithic silica body and the glass body are fused and integrated, and then the monolithic silica body and the glass body are subjected to chemical modification.

8. A separation medium prepared by coating a side surface of a rod-shaped monolithic silica body with a glass body, wherein the monolithic silica body and the glass body both have SiO2 as a main component and fusing the monolithic silica body and the glass body to integrate the two, and chemically bonding $SiO_2$ of the monolithic silica body and $SiO_2$ of the glass body with each other, thereby assimilating the monolithic silica body and the glass body with each other.

9. A separation medium according to claim 8, wherein the monolithic silica body has been additionally subjected to chemical modification.

10. The separation medium according to claim 9, wherein a protective layer is formed on the outside of the glass body.

11. The separation medium according to claim 10, wherein the protective layer comprises one member selected from metal and synthetic polymer or a mixture thereof.

12. The separation medium according to claim 10, wherein a coat layer is provided between the outside of the glass body and the protective layer.

13. The separation medium according to claim 12, wherein the coat layer contains a synthetic polymer.

14. The separation medium according to claim 8, wherein the separation medium is any one of an HPLC column, a GC column, a column for column chromatography, a column for pretreatment, a guard column, a cartridge for solid phase and a passive sampler.

15. The separation medium according to claim 8, wherein a protective layer is formed on the outside of the glass body.

16. The separation medium according to claim 15, wherein the protective layer comprises one member selected from metal and synthetic polymer or a mixture thereof.

17. The separation medium according to claim 15, wherein a coat layer is formed between the outside of the glass body and the protective layer.

18. The separation medium according to claim 17, wherein the coat layer contains a synthetic polymer.

19. The separation medium according to claim 8, wherein the monolithic silica body and the glass body are subjected to chemical modification.

20. A separation medium, wherein a side surface of a monolithic silica body molded into a rod shape is coated with a glass body having $SiO_2$ as the same main component as the monolithic silica body and the monolithic silica body and the glass body are fused and integrated, and $SiO_2$ of the monolithic silica body and $SiO_2$ of the glass body are chemically bonded with each other, and the monolithic silica body and the glass body are assimilated with each other.

* * * * *